US012692488B2

(12) United States Patent
Zheng et al.

(10) Patent No.: US 12,692,488 B2
(45) Date of Patent: Jul. 28, 2026

(54) CHIMERIC LYSOZYME VARIANT AND APPLICATION THEREOF IN ANIMAL FEED ADDITIVE

(71) Applicants: NANJING BESTZYME BIO-ENGINEERING CO., LTD., Nanjing (CN); JINAN BESTZYME BIO-ENGINEERING CO., LTD., Jinan (CN)

(72) Inventors: Fei Zheng, Nanjing (CN); Ting Yan, Nanjing (CN); Jidong Zhu, Nanjing (CN); Hong Xu, Nanjing (CN); Yan Sun, Nanjing (CN); Yanjie Liu, Jinan (CN)

(73) Assignees: NANJING BESTZYME BIO-ENGINEERING CO., LTD., Nanjing (CN); JINAN BESTZYME BIO-ENGINEERING CO., LTD., Jinan (CN)

( * ) Notice: Subject to any disclaimer, the term of this patent is extended or adjusted under 35 U.S.C. 154(b) by 517 days.

(21) Appl. No.: 18/254,428

(22) PCT Filed: Nov. 12, 2021

(86) PCT No.: PCT/CN2021/130202
§ 371 (c)(1),
(2) Date: May 25, 2023

(87) PCT Pub. No.: WO2022/111301
PCT Pub. Date: Jun. 2, 2022

(65) Prior Publication Data
US 2024/0093171 A1      Mar. 21, 2024

(30) Foreign Application Priority Data

Nov. 26, 2020    (CN) ......................... 202011346101.6
Apr. 28, 2021    (CN) ......................... 202110464931.7

(51) Int. Cl.
*C12N 9/36*        (2006.01)
*A23K 20/189*      (2016.01)

(52) U.S. Cl.
CPC .......... *C12N 9/2462* (2013.01); *A23K 20/189* (2016.05); *C12Y 302/01017* (2013.01)

(58) Field of Classification Search
CPC .......... C12N 9/2462; C12Y 302/01017; A23K 20/189
See application file for complete search history.

(56) References Cited

FOREIGN PATENT DOCUMENTS

| | | |
|---|---|---|
| CN | 102858968 A | 1/2013 |
| CN | 110072996 A | 7/2019 |
| CN | 110621779 A | 12/2019 |
| CN | 111787810 A | 10/2020 |
| WO | 2017000922 A1 | 1/2017 |
| WO | WO-2018206001 A1 * | 11/2018 ............. A23K 50/80 |

OTHER PUBLICATIONS

Result 3, SEQ ID No. 8 Search—WO 2018/206001—85.7% match to SEQ ID: 29 (Year: 2018).*
Berka, R.M. et al., "Comparative Genomic Analysis of the Thermophilic Biomass-Degrading Fungi Myceliophthora thermophila and Thielavia terrestris"; NCBI_Genbank., AEO64608.1; Sep. 2, 2014, Features, Origin; pp. 1-2.
Parent-Michaud, M. et al.; "Draft genome sequence of azole-resistant Aspergillus thermomutatus (Neosartorya pseudofischeri) strain HMR AF 39, isolated from a human nasal aspirate"; NCBI_Genbank; RHZ62009.1; Sep. 12, 2018; Features, Origin; pp. 1-2.
Biswas,Ashraf A. et al.; "Use of Lysozyme as a Feed Additive on In vitro Rumen Fermentation and Methane Emission."; Asian Australas. J. Anim. Sci., vol. 29, No. 11, Nov. 30, 2016, pp. 1601-1607.

* cited by examiner

*Primary Examiner* — Ruth A Davis
(74) *Attorney, Agent, or Firm* — NKL Law; Allen Xue

(57) ABSTRACT

A chimeric lysozyme variant has an improved heat resistance and is encoded by a polynucleotide. A novel chimeric lysozyme sequence is constructed, and high-efficiency expression in a host cell is achieved. The thermal stability of the chimeric lysozyme under the condition of 60° C. is nearly doubled compared to a parental sequence. The chimeric lysozyme variant can be used to prepare product that is antibiotic, for example, animal feed additive containing the chimeric lysozyme variant and an animal feed containing the animal feed additive.

12 Claims, 5 Drawing Sheets
Specification includes a Sequence Listing.

SEQUENCE LISTING

<160> NUMBER OF SEQ ID NOS: 20

<210> SEQ ID NO 1
<211> LENGTH: 2724
<212> TYPE: DNA
<213> ORGANISM: Artificial sequence
<220> FEATURE:
<223> OTHER INFORMATION: synthesized

<400> SEQUENCE: 1

```
ctagatctac gccaggaccg agcaagccca gatgagaacc gacgcagatt tccttggcac      60
ctgttgcttc agctgaatcc tggcaatacg agatacctgc tttgaatatt ttgaatagct     120
cgcccgctgg agagcatcct gaatgcaagt aacaaccgta gaggctgaca cggcaggtgt     180
tgctagggag cgtcgtgttc tacaaggcca gacgtcttcg cggttgatat atatgtatgt     240
ttgactgcag gctgctcagc gacgacagtc aagttcgccc tcgctgcttg tgcaataatc     300
gcagtgggga agccacaccg tgactccat ctttcagtaa agctctgttg gtgtttatca      360
gcaatacacg taatttaaac tcgttagcat ggggctgata gcttaattac cgtttaccag     420
tgccgcggtt ctgcagcttt ccttggcccg taaaattcgg cgaagccagc caatcaccag     480
ctaggcacca gctaaaccct ataattagtc tcttatcaac accatccgct cccccgggat     540
caatgaggag aatgagggg atgcggggct aaagaagcct acataaccct catgccaact     600
cccagtttac actcgtcgag ccaacatcct gactataagc taacacagaa tgcctcaatc     660
ctgggaagaa ctggccgctg ataagcgcgc ccgcctcgca aaaaccatcc ctgatgaatg     720
gaaagtccag acgctgcctg cggaagacag cgttattgat ttcccaaaga aatcggggat     780
cctttcagag gccgaactga agatcacaga ggcctccgct gcagatcttg tgtccaagct     840
ggcggccgga gagttgacct cggtggaagt tacgctagca ttctgtaaac gggcagcaat     900
cgcccagcag ttagtagggt cccctctacc tctcagggag atgtaacaac gccaccttat     960
gggactatca agctgacgct ggcttctgtg cagacaaact gcgcccacga gttcttccct    1020
gacgccgctc tcgcgcaggc aagggaactc gatgaatact acgcaaagca caagagaccc    1080
gttggtccac tccatggcct ccccatctct ctcaaagacc agcttcgagt caaggtacac    1140
cgttgcccct aagtcgttag atgtcccttt ttgtcagcta acatatgcca ccagggctac    1200
gaaacatcaa tgggctacat ctcatggcta aacaagtacg acgaagggga ctcggttctg    1260
acaaccatgc tccgcaaagc cggtgccgtc ttctacgtca agacctctgt cccgcagacc    1320
ctgatggtct gcgagacagt caacaacatc atcgggcgca ccgtcaaccc acgcaacaag    1380
aactggtcgt gcggcggcag ttctggtggt gagggtgcga tcgttgggat tcgtggtggc    1440
gtcatcggtg taggaacgga tatcggtggc tcgattcgag tgccggccgc gttcaacttc    1500
ctgtacggtc taaggccgag tcatgggcgg ctgccgtatg caaagatggc gaacagcatg    1560
gagggtcagg agacggtgca cagcgttgtc gggccgatta cgcactctgt tgagggtgag    1620
tccttcgcct cttccttctt ttcctgctct ataccaggcc tccactgtcc tcctttcttg    1680
ctttttatac tatatacgag accggcagtc actgatgaag tatgttagac ctccgcctct    1740
tcaccaaatc cgtcctcggt caggagccat ggaaatacga ctccaaggtc atccccatgc    1800
cctggcgcca gtccgagtcg acattattg cctccaagat caagaacggc gggctcaata    1860
tcggctacta caacttcgac ggcaatgtcc ttccacaccc tcctatcctg cgcggcgtgg    1920
aaaccaccgt cgccgcactc gccaaagccg gtcacaccgt gaccccgtgg acgccataca    1980
agcacgattt cggccacgat ctcatctccc atatctacgc ggctgacggc agcgccgacg    2040
```

-continued

```
taatgcgcga tatcagtgca tccggcgagc cggcgattcc aaatatcaaa gacctactga    2100
acccgaacat caaagctgtt aacatgaacg agctctggga cacgcatctc cagaagtgga    2160
attaccagat ggagtacctt gagaaatggc gggaggctga agaaaaggcc gggaaggaac    2220
tggacgccat catcgcgccg attacgccta ccgctgcggt acggcatgac cagttccggt    2280
actatgggta tgcctctgtg atcaacctgc tggatttcac gagcgtggtt gttccggtta    2340
cctttgcgga taagaacatc gataagaaga atgagagttt caaggcggtt agtgagcttg    2400
atgccctcgt gcaggaagag tatgatccgg aggcgtacca tggggcaccg gttgcagtgc    2460
aggttatcgg acggagactc agtgaagaga ggacgttggc gattgcagag gaagtgggga    2520
agttgctggg aaatgtggtg actccatagc taataagtgt cagatagcaa tttgcacaag    2580
aaatcaatac cagcaactgt aaataagcgc tgaagtgacc atgccatgct acgaaagagc    2640
agaaaaaaac ctgccgtaga accgaagaga tatgacacgc ttccatctct caaaggaaga    2700
atcccttcag ggttgcgttt ccag                                          2724
```

<210> SEQ ID NO 2
<211> LENGTH: 997
<212> TYPE: DNA
<213> ORGANISM: Artificial sequence
<220> FEATURE:
<223> OTHER INFORMATION: synthesized

<400> SEQUENCE: 2

```
gccattggcg gaggggtccg gacggtcagg aacttagcct tatgagatga atgatggacg      60
tgtctggcct cggaaaagga tatatgggga tcatgatagt actagccata ttaatgaagg     120
gcatatacca cgcgttggac ctgcgttata gcttcccgtt agttatagta ccatcgttat     180
accagccaat caagtcacca cgcacgaccg gggacggcga atccccggga attgaaagaa     240
attgcatccc aggccagtga ggccagcgat tggccacctc tccaaggcac agggccattc     300
tgcagcgctg gtggattcat cgcaatttcc cccggcccgg cccgacaccg ctataggctg     360
gttctcccac accatcggag attcgtcgcc taatgtctcg tccgttcaca agctgaagag     420
cttgaagtgg cgagatgtct ctgcaggaat tcaagctaga tgctaagcga tattgcatgg     480
caatatgtgt tgatgcatgt gcttcttcct tcagcttccc ctcgtgcaga tgaggtttgg     540
ctataaattg aagtggttgg tcggggttcc gtgaggggct gaagtgcttc ctccctttta     600
gacgcaactg agagcctgag cttcatcccc agcatcatta cacctcagca cttaagacta     660
gtacgcgtct cgagatctag agggtgactg acacctggcg gtagacaatc aatccatttc     720
gctatagtta aaggatgggg atgagggcaa ttggttatat gatcatgtat gtagtgggtg     780
tgcataatag tagtgaaatg gaagccaagt catgtgattg taatcgaccg acggaattga     840
ggatatccgg aaatacagac accgtgaaag ccatggtctt tccttcgtgt agaagaccag     900
acagacagtc cctgatttac ccttgcacaa agcactagaa aattagcatt ccatccttct     960
ctgcttgctc tgctgatatc actgtcattc aatgcat                             997
```

<210> SEQ ID NO 3
<211> LENGTH: 814
<212> TYPE: DNA
<213> ORGANISM: Artificial sequence
<220> FEATURE:
<223> OTHER INFORMATION: synthesized

<400> SEQUENCE: 3

-continued

```
atgttgtacc ttcctctcgt tgccctctcc tttgctgcca ccgttcctct ggtgagcgca      60
taccccatca ctggcgatgg tgtcaactgc cgctctggtc ctggcaccaa ccatgccgtg     120
gtcaagtctt accccaaggg ccatgagatc tccattgtct gccaggctgc cggcaccaac     180
gtcaagggag atgagctctg ggacaagacg tccgacggct gctatgtcgc cgattactac     240
gtgaagaccg gtaccactgg ctatgtcacc aagcactgcg atggcggcag tgatggtggc     300
agcggcggcg gcagcggcaa tcttcccggt ctcactgcca ctcagtcctc tcacgctcat     360
gcaatcatcg gtgaagcaaa gaaggaaggc ctgggtcgtc aaggctgtct ggctggtatt     420
gcaactggct tggtcgaggt gagtacctat tcctcttcat tgcatcggca attatgatca     480
ttgtactgat ggtgagctat tatagtccaa tcttttgatc tatgccaata gcaaggtacc     540
cgagtcgctc aaataccacc atgatgccgt cggccacgac tacgacagcg tgggcatctt     600
ccagcaacgt gctgtctact accccaacat cgctgctgac atggaccctg cacgctctgc     660
ggctcagttc tttgccaaga tgaagaatat cagcggctgg aagacgatgg atgtcggcaa     720
gctgtgccag aaggtgcagg tctccgccta ccccgatcgg tatgcgcaac gtgtgcctgc     780
tgctgagaag atctgcgctg ctggtggact gtag                                 814
```

```
<210> SEQ ID NO 4
<211> LENGTH: 248
<212> TYPE: PRT
<213> ORGANISM: Artificial sequence
<220> FEATURE:
<223> OTHER INFORMATION: synthesized

<400> SEQUENCE: 4

Met Leu Tyr Leu Pro Leu Val Ala Leu Ser Phe Ala Ala Thr Val Pro
1               5                   10                  15

Leu Val Ser Ala Tyr Pro Ile Thr Gly Asp Gly Val Asn Cys Arg Ser
                20                  25                  30

Gly Pro Gly Thr Asn His Ala Val Val Lys Ser Tyr Pro Lys Gly His
            35                  40                  45

Glu Ile Ser Ile Val Cys Gln Ala Ala Gly Thr Asn Val Lys Gly Asp
        50                  55                  60

Glu Leu Trp Asp Lys Thr Ser Asp Gly Cys Tyr Val Ala Asp Tyr Tyr
65                  70                  75                  80

Val Lys Thr Gly Thr Thr Gly Tyr Val Thr Lys His Cys Asp Gly Gly
                85                  90                  95

Ser Asp Gly Gly Ser Gly Gly Gly Ser Gly Asn Leu Pro Gly Leu Thr
            100                 105                 110

Ala Thr Gln Ser Ser His Ala His Ala Ile Ile Gly Glu Ala Lys Lys
        115                 120                 125

Glu Gly Leu Gly Arg Gln Gly Cys Leu Ala Gly Ile Ala Thr Gly Leu
        130                 135                 140

Val Glu Ser Asn Leu Leu Ile Tyr Ala Asn Ser Lys Val Pro Glu Ser
145                 150                 155                 160

Leu Lys Tyr His His Asp Ala Val Gly His Asp Tyr Asp Ser Val Gly
                165                 170                 175

Ile Phe Gln Gln Arg Ala Val Tyr Tyr Pro Asn Ile Ala Ala Asp Met
            180                 185                 190

Asp Pro Ala Arg Ser Ala Ala Gln Phe Phe Ala Lys Met Lys Asn Ile
        195                 200                 205

Ser Gly Trp Lys Thr Met Asp Val Gly Lys Leu Cys Gln Lys Val Gln
        210                 215                 220
```

-continued

```
Val Ser Ala Tyr Pro Asp Arg Tyr Ala Gln Arg Val Pro Ala Ala Glu
225                 230                 235                 240

Lys Ile Cys Ala Ala Gly Gly Leu
                245

<210> SEQ ID NO 5
<211> LENGTH: 838
<212> TYPE: DNA
<213> ORGANISM: Artificial sequence
<220> FEATURE:
<223> OTHER INFORMATION: synthesized

<400> SEQUENCE: 5
atgcagctct ccctcctcgt cctctccctc gtggccgctg tgcccatggc cagcgcgtac       60
ccggtcaagg ccgacactct caactgccgc tccggcccgg gcaccagtta caaggtcatc      120
aagacctaca agaagggcac cgatctcaag atcacctgcc agacgcccgg cacctcggtc      180
aacggcgaca acctgtggga caagacctcg gacggctgct acgtggccga ttactacgtc      240
aagaccggca cctccggcta cgtcacggcc cattgcgatg ccggcagcgg cagcggcagc      300
agcggcggcg gcaacctgcc aggactcaac tcggtccagt cctcgcacgc ccgggccatc      360
atcggcgagg cgaagaagga gggcgtcggc cgccacggct gcgaggccgg catcgcgacc      420
gcgcttgtcg aggtacgttg catcctaaca tcaacactta cttgccttga ccccactgtc      480
accgccagaa aaaccaaaa ctaacacatc acctcttccc ctcacacagt ccaacatcct      540
gatctacgcc aacaaggcgg tcccggcctc gctcaagtac ccgcacgacg cggtgggctc      600
ggaccacgac agcgtcggca tcttccagca gcgcgccaag tactacccca acatcgcggc      660
cgacatggac ccggcgcgct cggccgccca gttcttcgcc aagatgaagg gcatcaaggg      720
ctggcagagc atggccgtcg gcacgctctg ccagaaggtc cagggctccg cgtacccgga      780
ccgctatgcc aagcgggtct cggaggcgac caagatttgc caggctggtg ggttgtaa       838

<210> SEQ ID NO 6
<211> LENGTH: 246
<212> TYPE: PRT
<213> ORGANISM: Artificial sequence
<220> FEATURE:
<223> OTHER INFORMATION: synthesized

<400> SEQUENCE: 6

Met Gln Leu Ser Leu Leu Val Leu Ser Leu Val Ala Ala Val Pro Met
1               5                   10                  15

Ala Ser Ala Tyr Pro Val Lys Ala Asp Thr Leu Asn Cys Arg Ser Gly
                20                  25                  30

Pro Gly Thr Ser Tyr Lys Val Ile Lys Thr Tyr Lys Lys Gly Thr Asp
            35                  40                  45

Leu Lys Ile Thr Cys Gln Thr Pro Gly Thr Ser Val Asn Gly Asp Asn
        50                  55                  60

Leu Trp Asp Lys Thr Ser Asp Gly Cys Tyr Val Ala Asp Tyr Tyr Val
65                  70                  75                  80

Lys Thr Gly Thr Ser Gly Tyr Val Thr Ala His Cys Asp Ala Gly Ser
                85                  90                  95

Gly Ser Gly Ser Ser Gly Gly Gly Asn Leu Pro Gly Leu Asn Ser Val
            100                 105                 110

Gln Ser Ser His Ala Arg Ala Ile Ile Gly Glu Ala Lys Lys Glu Gly
        115                 120                 125
```

-continued

```
Val Gly Arg His Gly Cys Glu Ala Gly Ile Ala Thr Ala Leu Val Glu
    130             135             140

Ser Asn Ile Leu Ile Tyr Ala Asn Lys Ala Val Pro Ala Ser Leu Lys
145             150             155             160

Tyr Pro His Asp Ala Val Gly Ser Asp His Asp Ser Val Gly Ile Phe
            165             170             175

Gln Gln Arg Ala Lys Tyr Tyr Pro Asn Ile Ala Ala Asp Met Asp Pro
            180             185             190

Ala Arg Ser Ala Ala Gln Phe Phe Ala Lys Met Lys Gly Ile Lys Gly
        195             200             205

Trp Gln Ser Met Ala Val Gly Thr Leu Cys Gln Lys Val Gln Gly Ser
    210             215             220

Ala Tyr Pro Asp Arg Tyr Ala Lys Arg Val Ser Glu Ala Thr Lys Ile
225             230             235             240

Cys Gln Ala Gly Gly Leu
            245
```

```
<210> SEQ ID NO 7
<211> LENGTH: 844
<212> TYPE: DNA
<213> ORGANISM: Artificial sequence
<220> FEATURE:
<223> OTHER INFORMATION: synthesized

<400> SEQUENCE: 7
atgttgtacc ttcctctcgt tgccctctcc tttgctgcca ccgttcctct ggtgagcgca      60
taccccatca ctggcgatgg tgtcaactgc cgctctggtc ctggcaccaa ccatgccgtg     120
gtcaagtctt accccaaggg ccatgagatc tccattgtct gccaggctgc cggcaccaac     180
gtcaagggag atgagctctg ggacaagacg tccgacggct gctatgtcgc cgattactac     240
gtgaagaccg gtaccactgg ctatgtcacc aagcactgcg atggcggcag tgatggtggc     300
agcggcggcg gcagcggcaa tcttcccggt ctcaactcgg tccagtcctc gcacgcccgg     360
gccatcatcg gcgaggcgaa gaaggagggc gtcggccgcc acggctgcga ggccggcatc     420
gcgaccgcgc ttgtcgaggt acgttgcatc ctaacatcaa cacttacttg ccttgacccc     480
actgtcaccg ccagaaaaaa ccaaaactaa cacatcacct cttcccctca cacagtccaa     540
catcctgatc tacgccaaca aggcggtccc ggcctcgctc aagtacccgc acgacgcggt     600
gggctcggac cacgacagcg tcggcatctt ccagcagcgc gccaagtact accccaacat     660
cgcggccgac atggacccgg cgcgctcggc cgcccagttc ttcgccaaga tgaagggcat     720
caagggctgg cagagcatgg ccgtcggcac gctctgccag aaggtccagg gctccgcgta     780
cccggaccgc tatgccaagc gggtctcgga ggcgaccaag atttgccagg ctggtgggtt     840
gtaa                                                                   844
```

```
<210> SEQ ID NO 8
<211> LENGTH: 248
<212> TYPE: PRT
<213> ORGANISM: Artificial sequence
<220> FEATURE:
<223> OTHER INFORMATION: synthesized

<400> SEQUENCE: 8

Met Leu Tyr Leu Pro Leu Val Ala Leu Ser Phe Ala Ala Thr Val Pro
1               5               10              15

Leu Val Ser Ala Tyr Pro Ile Thr Gly Asp Gly Val Asn Cys Arg Ser
            20              25              30
```

```
Gly Pro Gly Thr Asn His Ala Val Val Lys Ser Tyr Pro Lys Gly His
      35                  40                  45

Glu Ile Ser Ile Val Cys Gln Ala Ala Gly Thr Asn Val Lys Gly Asp
   50                  55                  60

Glu Leu Trp Asp Lys Thr Ser Asp Gly Cys Tyr Val Ala Asp Tyr Tyr
65                  70                  75                  80

Val Lys Thr Gly Thr Thr Gly Tyr Val Thr Lys His Cys Asp Gly Gly
               85                  90                  95

Ser Asp Gly Gly Ser Gly Gly Gly Ser Gly Asn Leu Pro Gly Leu Asn
               100                 105                 110

Ser Val Gln Ser Ser His Ala Arg Ala Ile Ile Gly Glu Ala Lys Lys
               115                 120                 125

Glu Gly Val Gly Arg His Gly Cys Glu Ala Gly Ile Ala Thr Ala Leu
      130                 135                 140

Val Glu Ser Asn Ile Leu Ile Tyr Ala Asn Lys Ala Val Pro Ala Ser
145                 150                 155                 160

Leu Lys Tyr Pro His Asp Ala Val Gly Ser Asp His Asp Ser Val Gly
               165                 170                 175

Ile Phe Gln Gln Arg Ala Lys Tyr Tyr Pro Asn Ile Ala Ala Asp Met
               180                 185                 190

Asp Pro Ala Arg Ser Ala Ala Gln Phe Phe Ala Lys Met Lys Gly Ile
               195                 200                 205

Lys Gly Trp Gln Ser Met Ala Val Gly Thr Leu Cys Gln Lys Val Gln
      210                 215                 220

Gly Ser Ala Tyr Pro Asp Arg Tyr Ala Lys Arg Val Ser Glu Ala Thr
225                 230                 235                 240

Lys Ile Cys Gln Ala Gly Gly Leu
               245
```

```
<210> SEQ ID NO 9
<211> LENGTH: 23
<212> TYPE: DNA
<213> ORGANISM: Artificial sequence
<220> FEATURE:
<223> OTHER INFORMATION: synthesized

<400> SEQUENCE: 9
cttggcgtaa tcatggtcat agc                                          23

<210> SEQ ID NO 10
<211> LENGTH: 40
<212> TYPE: DNA
<213> ORGANISM: Artificial sequence
<220> FEATURE:
<223> OTHER INFORMATION: synthesized

<400> SEQUENCE: 10
cggacccctc cgccaatggc cttgcatgca ggcctctgca                        40

<210> SEQ ID NO 11
<211> LENGTH: 20
<212> TYPE: DNA
<213> ORGANISM: Artificial sequence
<220> FEATURE:
<223> OTHER INFORMATION: synthesized

<400> SEQUENCE: 11
ctagatctac gccaggaccg                                              20
```

<210> SEQ ID NO 12
<211> LENGTH: 40
<212> TYPE: DNA
<213> ORGANISM: Artificial sequence
<220> FEATURE:
<223> OTHER INFORMATION: synthesized

<400> SEQUENCE: 12
atgaccatga ttacgccaag cttctggaaa cgcaaccctg                          40

<210> SEQ ID NO 13
<211> LENGTH: 20
<212> TYPE: DNA
<213> ORGANISM: Artificial sequence
<220> FEATURE:
<223> OTHER INFORMATION: synthesized

<400> SEQUENCE: 13
gccattggcg gaggggtccg                                                20

<210> SEQ ID NO 14
<211> LENGTH: 40
<212> TYPE: DNA
<213> ORGANISM: Artificial sequence
<220> FEATURE:
<223> OTHER INFORMATION: synthesized

<400> SEQUENCE: 14
cggtcctggc gtagatctag atgcattgaa tgacagtgat                          40

<210> SEQ ID NO 15
<211> LENGTH: 52
<212> TYPE: DNA
<213> ORGANISM: Artificial sequence
<220> FEATURE:
<223> OTHER INFORMATION: synthesized

<400> SEQUENCE: 15
catccccagc atcattacac ctcagcaatg ttgtaccttc ctctcgttgc cc            52

<210> SEQ ID NO 16
<211> LENGTH: 55
<212> TYPE: DNA
<213> ORGANISM: Artificial sequence
<220> FEATURE:
<223> OTHER INFORMATION: synthesized

<400> SEQUENCE: 16
aggtgtcagt caccctctag atctcgagct acagtccacc agcagcgcag atctt         55

<210> SEQ ID NO 17
<211> LENGTH: 48
<212> TYPE: DNA
<213> ORGANISM: Artificial sequence
<220> FEATURE:
<223> OTHER INFORMATION: synthesized

<400> SEQUENCE: 17
catccccagc atcattacac ctcagcaatg cagctctccc tcctcgtc                 48

<210> SEQ ID NO 18
<211> LENGTH: 52
<212> TYPE: DNA
<213> ORGANISM: Artificial sequence
<220> FEATURE:
<223> OTHER INFORMATION: synthesized

<400> SEQUENCE: 18
gtgtcagtca ccctctagat ctcgagttac aacccaccag cctggcaaat ct                52

<210> SEQ ID NO 19
<211> LENGTH: 808
<212> TYPE: DNA
<213> ORGANISM: Artificial sequence
<220> FEATURE:
<223> OTHER INFORMATION: synthesized

<400> SEQUENCE: 19
atgcagctct ccctcctcgt cctctccctc gtggccgctg tgcccatggc cagcgcgtac     60
ccggtcaagg ccgacactct caactgccgc tccggcccgg gcaccagtta caaggtcatc     120
aagacctaca agaagggcac cgatctcaag atcacctgcc agacgcccgg cacctcggtc     180
aacggcgaca acctgtggga caagacctcg gacggctgct acgtggccga ttactacgtc     240
aagaccggca cctccggcta cgtcacggcc cattgcgatg ccggcagcgg cagcggcagc     300
agcggcggcg gcaacctgcc aggactcact gccactcagt cctctcacgc tcatgcaatc     360
atcggtgaag caaagaagga aggcctgggt cgtcaaggct gtctggctgg tattgcaact     420
ggcttggtcg aggtgagtac ctattcctct tcattgcatc ggcaattatg atcattgtac     480
tgatggtgag ctattatagt ccaatctttt gatctatgcc aatagcaagg tacccgagtc     540
gctcaaatac caccatgatg ccgtcggcca cgactacgac agcgtgggca tcttccagca     600
acgtgctgtc tactacccca acatcgctgc tgacatggac cctgcacgct ctgcggctca     660
gttctttgcc aagatgaaga atatcagcgg ctggaagacg atggatgtcg gcaagctgtg     720
ccagaaggtg caggtctccg cctaccccga tcggtatgcg caacgtgtgc ctgctgctga     780
gaagatctgc gctgctggtg gactgtag                                       808

<210> SEQ ID NO 20
<211> LENGTH: 246
<212> TYPE: PRT
<213> ORGANISM: Artificial sequence
<220> FEATURE:
<223> OTHER INFORMATION: synthesized

<400> SEQUENCE: 20

Met Gln Leu Ser Leu Leu Val Leu Ser Leu Val Ala Ala Val Pro Met
1               5                   10                  15

Ala Ser Ala Tyr Pro Val Lys Ala Asp Thr Leu Asn Cys Arg Ser Gly
                20                  25                  30

Pro Gly Thr Ser Tyr Lys Val Ile Lys Thr Tyr Lys Lys Gly Thr Asp
            35                  40                  45

Leu Lys Ile Thr Cys Gln Thr Pro Gly Thr Ser Val Asn Gly Asp Asn
        50                  55                  60

Leu Trp Asp Lys Thr Ser Asp Gly Cys Tyr Val Ala Asp Tyr Tyr Val
65                  70                  75                  80

Lys Thr Gly Thr Ser Gly Tyr Val Thr Ala His Cys Asp Ala Gly Ser
                85                  90                  95

Gly Ser Gly Ser Ser Gly Gly Gly Asn Leu Pro Gly Leu Thr Ala Thr
                100                 105                 110

Gln Ser Ser His Ala His Ala Ile Ile Gly Glu Ala Lys Lys Glu Gly
            115                 120                 125

Leu Gly Arg Gln Gly Cys Leu Ala Gly Ile Ala Thr Gly Leu Val Glu
        130                 135                 140

-continued

```
Ser Asn Leu Leu Ile Tyr Ala Asn Ser Lys Val Pro Glu Ser Leu Lys
145             150             155             160

Tyr His His Asp Ala Val Gly His Asp Tyr Asp Ser Val Gly Ile Phe
                165             170             175

Gln Gln Arg Ala Val Tyr Tyr Pro Asn Ile Ala Ala Asp Met Asp Pro
            180             185             190

Ala Arg Ser Ala Ala Gln Phe Phe Ala Lys Met Lys Asn Ile Ser Gly
        195             200             205

Trp Lys Thr Met Asp Val Gly Lys Leu Cys Gln Lys Val Gln Val Ser
    210             215             220

Ala Tyr Pro Asp Arg Tyr Ala Gln Arg Val Pro Ala Ala Glu Lys Ile
225             230             235             240

Cys Ala Ala Gly Gly Leu
                245
```

CHIMERIC LYSOZYME VARIANT AND APPLICATION THEREOF IN ANIMAL FEED ADDITIVE

INCORPORATION OF SEQUENCE LISTING

This application contains a sequence listing submitted in Computer Readable Form (CRF) The CFR file contains the sequence listing entitled "PA150-0215_ST25.txt", which was created on May 19, 2023, and is 21,073 bytes in size. The information in the sequence listing is incorporated herein by reference in its entirety.

TECHNICAL FIELD

The present invention falls within the technical field of bioengineering, and relates to a chimeric lysozyme variant and an application thereof in an animal feed additive.

BACKGROUND ART

Lysozyme (EC 3.2.1.17) is a hydrolytic enzyme acting on the cell wall of microorganisms, also known as muramidase. It can effectively hydrolyze the peptidoglycan of the bacterial cell wall, which is mainly achieved by the mechanism of hydrolysis of the β-1,4 glycosidic bond between N-acetyl-muramic acid and N-acetylglucosamine to break the peptidoglycan backbone structure, resulting in cell wall rupture and eventually bacteriolysis.

Lysozyme naturally exists in many organisms, such as viruses, plants, insects, birds, reptiles and mammals. In mammals, lysozyme has been isolated from nasal secretions, saliva, tears, intestinal contents, urine and milk. At present, lysozyme has been classified into seven different glycoside hydrolase families (CAZy www.cazy.org): GH18, GH19, egg white lysozyme (GH22), goose egg white lysozyme (GH23), bacteriophage T4 lysozyme (GH24), *Sphingomonas* flagellin (GH73) and *Chalaropsis* lysozyme (GH25). Lysozyme is a non-toxic protein that has no side effects on humans and mammals. It has been widely used in various industries in recent years due to its bacteriolytic properties. Lysozyme can be used as a natural preservative in dairy industry. For example, adding lysozyme to pasteurized milk can effectively prolong its shelf life. In food applications, adding lysozyme can prolong the storage time of aquatic products and meat foods. In animal feed industry, the long-term and considerable use of antibiotics has had serious negative effects, manifested in increasingly serious drug resistance in livestock and poultry, and the emergence of a large number of highly drug-resistant strains and even new pathogenic strains, which not only makes the prevention and control of animal epidemic diseases more difficult, but also seriously affects the quality and safety of livestock and poultry products and directly threatens human health. The international community has recognized the harm of antibiotics, and many countries have begun to prohibit the addition of antibiotics to livestock and poultry feeds. In this context, lysozyme, as a non-specific immune factor, has an important application prospect in alternatives to antibiotics. Lysozyme can catalyze the hydrolysis of the β-1,4 glycosidic bond between N-acetylmuramic acid and N-acetylglucosamine in the bacterial cell wall, which leads to the exudation of bacterial contents and the lysis of bacteria, thus achieving effects such as antibacterial. Moreover, lysozyme can effectively decompose the pus of injured tissues and enhance the defense function, thus effectively protecting the digestive tract lining and accelerating the repair of the intestinal tract and injured tissues. In addition, lysozyme used in combination with polyphosphate and glycine has a good preservative effect. Adding lysozyme to feeds can prevent mildew, prolong the storage period of feeds and reduce unnecessary losses. The combination of lysozyme and glucose oxidase also provides a synergistic effect.

Currently, the application of lysozyme in feed and breeding production industries is greatly limited. The main reasons are as follows: one is that, currently, a significant proportion of the lysozyme is extracted from egg white, resulting in low productivity and output, as well as high costs; the other is that, most of the lysozyme has poor thermal stability and cannot meet the process requirements of high-temperature granulation of feeds. Therefore, it is of great significance to research and develop new lysozyme products obtained by microbial fermentation with lower cost and improved thermal stability.

SUMMARY OF THE INVENTION

To solve the above-mentioned technical problems, an objective of the present invention is to provide a chimeric lysozyme variant having improved heat resistance and a polynucleotide encoding same. A novel chimeric lysozyme variant sequence is constructed, and high-efficiency expression thereof in a host cell is achieved. The thermal stability of the chimeric lysozyme variant under the condition of 60° C. is nearly doubled compared to a parental sequence. Another objective of the present invention is to provide an application of a chimeric lysozyme variant having improved heat resistance in an animal feed additive. The feed additive has a significant effect on animal growth performance and greatly improves the conversion rate of the feed.

The present invention provides a chimeric lysozyme variant, wherein the chimeric lysozyme variant has an amino acid sequence set forth in SEQ ID NO: 8, or having at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 8; and the chimeric lysozyme variant has a lysozyme activity.

In a preferred embodiment, the amino acid sequence is set forth in SEQ ID NO: 8, that is, the amino acid sequence is obtained by substituting the first 109 amino acids at the N-terminus of the amino acid sequence set forth in SEQ ID NO: 6 with the first 111 amino acids at the N-terminus of the amino acid sequence set forth in SEQ ID NO: 4.

The present invention also provides the use of the chimeric lysozyme variant in the preparation of a product as an alternative to an antibiotic. The "product as an alternative to an antibiotic" refers to a product that can substitute an antibiotic, which can be used in an animal feed additive as a potential substitute for an antibiotic to inhibit the reproduction of harmful microorganisms, protect the animal intestinal health, and improve the animal immunity.

The present invention also provides the use of the chimeric lysozyme variant as described above, wherein the use is:

in an animal feed;
in an animal feed additive;
in the preparation of a composition for use in an animal feed;
for improving the nutritional value of an animal feed;
for improving the digestibility of an animal feed; and/or
for improving one or more performance parameters of an animal.

The present invention also provides a method for improving the nutritional value of an animal feed, comprising adding the chimeric lysozyme variant as described above to the feed.

The present invention also provides an animal feed additive, which comprises the chimeric lysozyme variant as described above.

Further, the feed additive comprises one or more components selected from the group consisting of:

one or more vitamins;

one or more minerals;

one or more amino acids;

one or more phytochemicals;

one or more prebiotics;

one or more organic acids; and one or more other feed ingredients.

The vitamins include fat-soluble vitamins and water-soluble vitamins. Non-limiting examples of the fat-soluble vitamins include vitamin A, vitamin D3, vitamin E and vitamin K, e.g., vitamin K3. Non-limiting examples of the water-soluble vitamins include vitamin C, vitamin B12, biotin and choline, vitamin B1, vitamin B2, vitamin B6, nicotinic acid, folic acid and pantothenate, e.g., Ca-D-pantothenate.

Non-limiting examples of the minerals include calcium, magnesium, phosphorus, potassium, sodium, boron, cobalt, chloride, chromium, copper, fluoride, iodine, iron, manganese, molybdenum, selenium and zinc.

Non-limiting examples of the amino acids are lysine, alanine, beta-alanine, threonine, methionine and tryptophan.

The phytochemicals are a group of natural growth promoters or non-antibiotic growth promoters derived from herbs, spices or other plants used as feed additives. Phytochemicals can be single substances prepared from essential oils/extracts, single plants and mixtures of plants (herbal products) or mixtures of essential oils/extracts/plants (specialized products). Examples of the phytochemicals are rosemary, sage, oregano, thyme, clove and lemongrass. Examples of the essential oils are thymol, eugenol, m-cresol, vanillin, salicylate, resorcinol, guajacol, gingerol, lavender oil, ionone, irone, cineole, menthol, peppermint oil, alpha-pinene, limonene, anethole, linalool, methyl dihydrojasmonate, carvacrol, propionic acid/propionate, acetic acid/acetate, butyric acid/butyrate, rosemary oil, clove oil, geraniol, terpineol, citronellol, amyl salicylate and/or benzyl salicylate, cinnamaldehyde, plant polyphenol (tannin), turmeric and turmeric extract.

The prebiotics are substances that induce the growth or activity of microorganisms (for example, bacteria and fungi), which contribute to the well-being of their host. Prebiotics are typically non-digestible fiber ingredients that pass through the upper part of the gastrointestinal tract without being digested. They stimulate the growth or activity of beneficial bacteria that colonize in the large intestine by serving as a substrate for these bacteria. Generally, prebiotics increase the number or activity of *Bifidobacteria* and lactic acid bacteria in the gastrointestinal (GI) tract. Yeast derivatives (inactivated whole yeast or yeast cell wall) can also be considered as prebiotics. They generally include mannooligosaccharides, yeast glucan or protein contents, and are generally derived from the cell wall of yeast (*Saccharomyces cerevisiae*).

The organic acids are widely distributed in nature as normal components of plant or animal tissues. They are also formed by microbial fermentation of carbohydrates mainly in the large intestine. Generally, the organic acids are used as substitutes for antibiotic growth promoters in pig and poultry production due to their preventive effect on intestinal problems such as necrotic enteritis in chickens and *Escherichia coli* infection in piglets. Organic acids can be sold as a single component or generally as a mixture of two or three different organic acids. Examples of the organic acids are propionic acid, formic acid, citric acid, lactic acid, sorbic acid, malic acid, acetic acid, fumaric acid, benzoic acid, butyric acid and tartaric acid or salts thereof (generally sodium or potassium salts, such as potassium dicarboxylate or sodium butyrate).

The feed additive of the present invention may further comprise colorants, stabilizers, growth improving additives and aromatic compounds/flavorings, polyunsaturated fatty acids (PUFAs), reactive oxygen generating substances, anti-oxidants, antimicrobial peptides, antifungal polypeptides and mycotoxin control compounds.

In a preferred embodiment, the chimeric lysozyme variant is added in an amount of 100-1000 g chimeric lysozyme variant per ton of animal feed (100-1000 g/t); preferably, the chimeric lysozyme variant is added in an amount of 250-500 g chimeric lysozyme variant per ton of animal feed (250-500 g/t).

The present invention also provides an animal feed containing the animal feed additive as described above.

Further, the feed contains basal diet.

The basal diet is formulated separately according to different growth stages as guided by Nutritional Requirements of Chicken of NRC (1994), Feeding Standard of Chicken in China (2004) and Tables of Feed Composition and Nutritive Values in China (2020).

In a preferred embodiment, the animal feed additive is added in an amount of 250-500 g animal feed additive per ton of animal feed (250-500 g/t).

Lysozyme is a non-toxic natural protein, and is a highly safe feed additive. Without any antibiotics, the addition of a lysozyme preparation to a feed can promote the digestion and absorption of nutrients by animals, improve the weight gain and feed conversion rate of animals, and reduce the morbidity and mortality of animals.

The present invention also provides a polynucleotide encoding the chimeric lysozyme variant as described above.

In a preferred embodiment, the polynucleotide has a nucleotide sequence set forth in SEQ ID NO: 7.

The present invention also provides a recombinant vector containing the polynucleotide encoding the chimeric lysozyme variant as described above.

The present invention also provides a host cell containing the recombinant vector as described above.

The host cell can be any of the *Aspergillus niger, Pichia pastoris, Aspergillus oryzae, Trichoderma reesei, Bacillus subtilis, Bacillus licheniformis* or *Escherichia coli*. The present invention has no specific limitations on the types of the host cell, so long as the chimeric lysozyme variant of the present invention can be successfully expressed by conventional experimental methods.

The present invention also provides a method for shake flask culture of a recombinant expression strain formed by lysozyme and *Aspergillus niger*, comprising inoculating a shake flask containing a YPM culture medium with lysozyme positive transformants, culturing same on a shaker and centrifuging same to collect a supernatant of the fermentation broth, and determining the enzyme activity of the lysozyme.

The YPM culture medium contains the following components with content in percent: yeast extract 0.2%, peptone 0.2%, and maltose 2%. The culture on a shaker is carried out at a temperature of 30-35° C.; preferably, 34° C.

The culture on a shaker is carried out at a rotating speed of 180-250 rpm; preferably, 220 rpm.

The culture on a shaker lasts for 4-6 days; preferably, 5 days.

The specific meanings of the following terms are shown below.

Sequence identity: the percent sequence identity is determined by a computer program based on a dynamic programming algorithm. Preferred computer programs within the scope of the present invention include the BLAST (Basic Local Alignment Search Tool) search program designed to explore all available sequence databases, regardless of whether the query is for protein or DNA. The BLAST version 2.0 of this search tool (Gapped BLAST) has been publicly available on the Internet (currently in http://www.ncbi.nlm.nih.gov/BLAST/). It uses an exploratory algorithm to search for local alignment instead of global alignment, enabling detection of the relationship between sequences that only share separated regions. Scores specified in the BLAST search have well-defined statistical explanations. The program preferably runs with selectable parameters set as default values.

Transformation refers to the introduction of an exogenous nucleic acid into a cell. In particular, it refers to the stable integration of a DNA molecule into the genome of a target organism.

Chimeric lysozyme variant refers to a polypeptide comprising domains from two or more polypeptides, for example, a binding domain from one polypeptide and a catalytic domain from another polypeptide. Domains can be fused at the N-terminus or C-terminus.

Lysozyme positive transformant specifically refers to a recombinant expression strain formed by transforming an expression plasmid containing a lysozyme sequence into a host strain, such as the recombinant expression strain formed by transforming the lysozyme lyzAth-amdS expression plasmid into a host *Aspergillus niger* as mentioned in example 2 of the present invention.

Lysozyme activity means bacteriolysis resulting from hydrolysis of the 1,4-β-bond between N-acetylmuramic acid and N-acetyl-D-glucosamine residues in peptidoglycan or between N-acetyl-D-glucosamine residues in chitodextrin. Lysozyme belongs to the class of enzymes EC3.2.1.17. The lysozyme activity is generally measured by turbidimetry, such as turbidity changes in a suspension of *Micrococcus luteus* CICC10680 as induced by bacteriolysis of the lysozyme. Under appropriate experimental conditions, these changes are proportional to the amount of lysozyme in a culture medium (c.f. INS 1105 of the Combined Compendium of Food Additive Specification of the Food and Agriculture Organization of the United Nations (www.fao.org)).

Heat resistance refers to the lysozyme activity after a period of incubation at an elevated temperature relative to the parental or reference sequence, either in a buffer or under conditions such as those that may be encountered during product storage/transport or conditions similar to those that exist during industrial use of the variant.

Animal feed refers to any compound, preparation or mixture suitable for or intended for intake by animals. Animal feeds for monogastric animals usually comprise concentrates as well as vitamins, minerals, enzymes, direct-fed microorganisms, amino acids and/or other feed ingredients (for example, in premixes), whereas animal feeds for ruminants usually comprises forage (including coarse grains and silage) and may further comprise concentrates as well as vitamins, minerals, enzymes, direct-fed microorganisms, amino acids and/or other feed ingredients (for example, in premixes).

The beneficial effects of the present invention are as follows. In the present invention, a novel chimeric lysozyme variant sequence is constructed, and high-efficiency expression thereof in *Aspergillus niger* is achieved. The heat resistance of the chimeric lysozyme variant sequence is remarkably improved compared to a parental sequence. In addition, based on the present invention, a new lysozyme product can be developed, which can bring a brand-new solution to protection of the animal intestinal health and improvement of the feed utilization rate under the background of "reducing and substituting antibiotics" in the national feed industry, and can be applied commercially.

DETAILED DESCRIPTION OF EMBODIMENTS

The present invention will be further illustrated in detail in conjunction with the following specific examples and drawings. Except for the content specifically mentioned below, the process, conditions, experimental methods, etc. used when implementing the present invention are all common knowledge and common sense in the art, and the present invention has no particular limitations on the content.

Example 1. Construction of Lysozyme Expression Plasmid, Including the Following Parts (1) a pUC57 plasmid was linearized with vector-F and vector-R primers;
(2) a marker amdS expression cassette was selected, which was synthesized by GenScript company, and had a sequence set forth in SEQ ID NO: 1;
(3) a DNA fragment containing the promoter and terminator of glucoamylase gene gla of *Aspergillus niger* was synthesized by GenScript company, and had a sequence set forth in SEQ ID NO: 2;
(4) lysozyme gene sequences:
lysozyme lyzAth (having a nucleotide sequence set forth in SEQ ID NO: 3 and an amino acid sequence set forth in SEQ ID NO: 4) derived from *Aspergillus thermomutatus;*
lysozyme lyzTte (having a nucleotide sequence as set forth SEQ ID NO: 5 and an amino acid sequence set forth in SEQ ID NO: 6) derived from *Thermothielavioides terrestris;*
the first 109 amino acids at the N-terminus of the amino acid sequence of lysozyme lyzTte derived from *Thermothielavioides terrestris* (set forth in SEQ ID NO: 6) were substituted with the first 111 amino acids at the N-terminus of the amino acid sequence of lysozyme lyzAth derived from *Aspergillus thermomutatus* (set forth in SEQ ID NO: 4) to obtain the chimeric lysozyme variant lyzAT (having a nucleotide sequence set forth in SEQ ID NO: 7 and an amino acid sequence set forth in SEQ ID NO: 8);

the first 111 amino acids at the N-terminus of the amino
acid sequence of lysozyme lyzAth derived from *Aspergillus thermomutatus* (set forth in SEQ ID NO: 4) were
substituted with the first 109 amino acids at the N-terminus of the amino acid sequence of lysozyme lyzTte
derived from *Thermothielavioides terrestris* (set forth
in SEQ ID NO: 6) to obtain the chimeric lysozyme
variant lyzTA (having a nucleotide sequence set forth in
SEQ ID NO: 19 and an amino acid sequence set forth
in SEQ ID NO: 20);

and the above-mentioned gene sequences were synthesized by GenScript company.

Firstly, primers amdS-F and amdS-R, and gla-F and gla-R
were used for PCR amplification to obtain an amdS gene
with a recombinant arm and a DNA fragment containing gla
promoter and terminator, respectively. The above-mentioned
linearized pUC57 plasmid, amdS gene and DNA fragment
containing gla promoter and terminator were recombined by
using Gbson Master Mix Kit (E2611, New England Biolabs)
to obtain a pGla-amdS plasmid, which was sequenced to
confirm the correct sequences. The plasmid could be linearized at an AflII site and then used for insertion of the
lysozyme gene.

Figure 3:
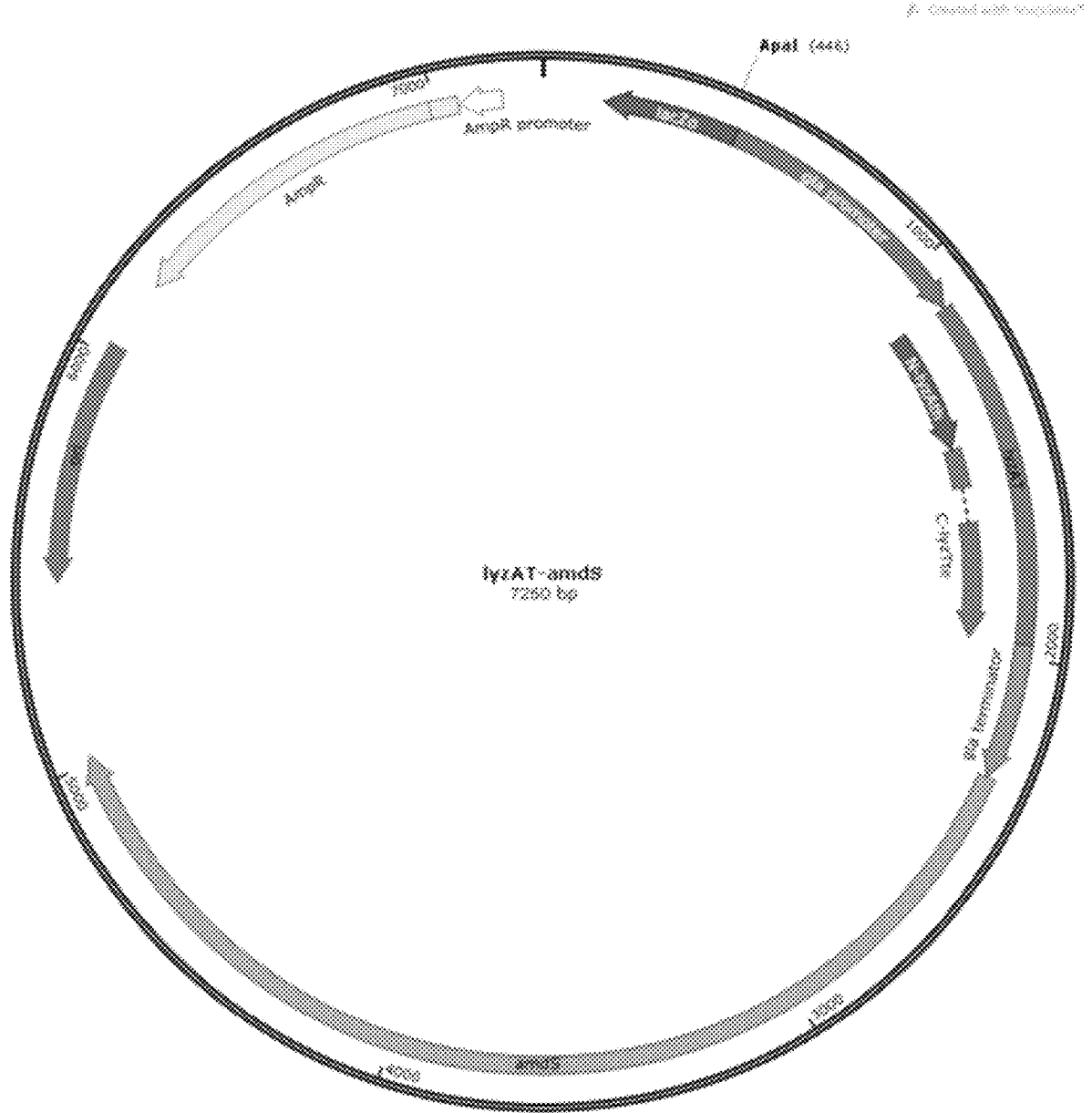
FIG. 3 is a map of lysozyme lyzAT expression plasmid.

The lysozyme lyzAT expression plasmid was constructed
as follows: primers lyzAth-F and lyzTte-R were used for
PCR amplification to obtain a lyzAT gene with a recombinant arm, and then the lyzAT gene was recombined with the
linearized pGla-amdS plasmid by using Gibson Master Mix
Kit (E2611, New England Biolabs) to obtain a plyzAT-amdS
plasmid, which was sequenced to confirm the sequences.
The map of the constructed plasmid was as shown in FIG.
3. The plasmid could be linearized at an ApaI site and then
used for protoplast transformation.

Figure 4:
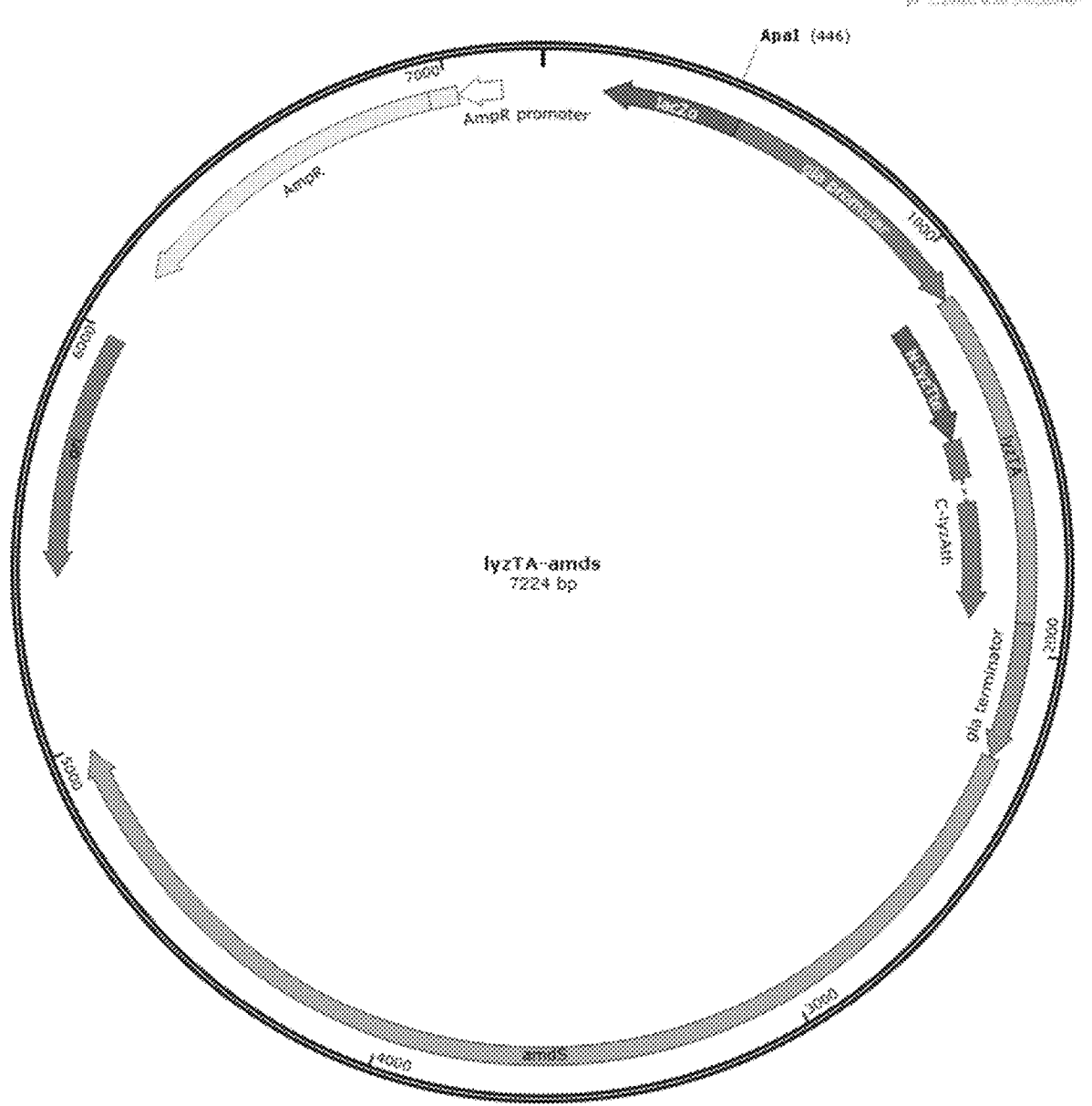
FIG. 4 is a map of lysozyme lyzTA expression plasmid.
Figure 5:
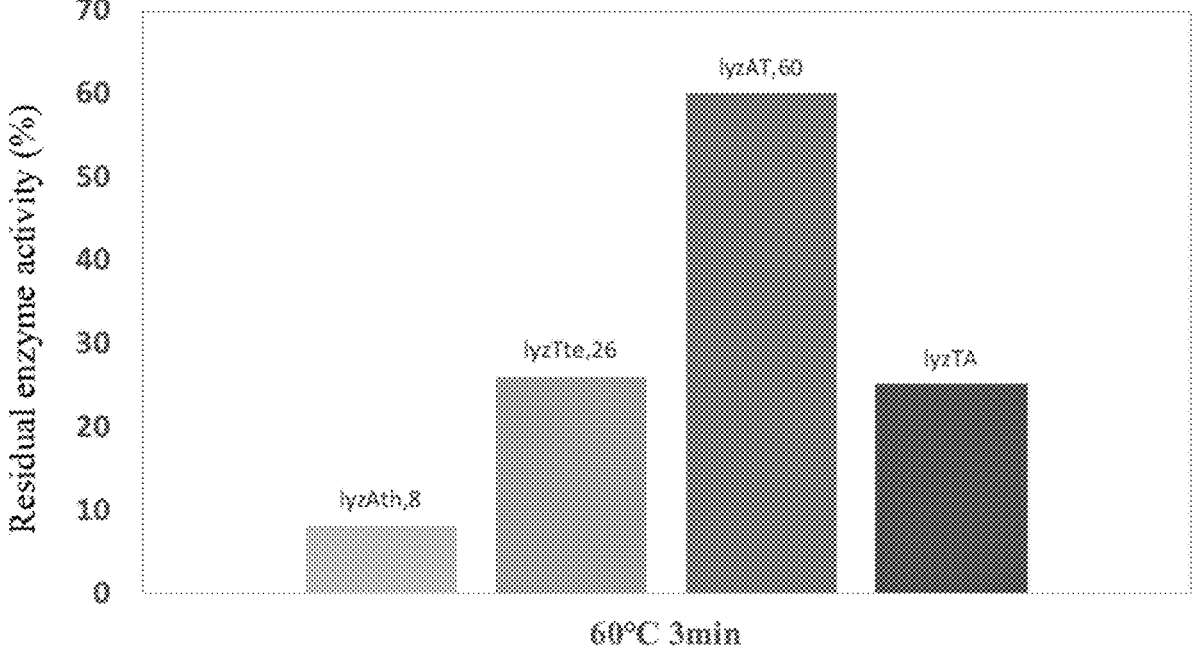
FIG. 5 shows the residual enzyme activity of three lysozymes after water bath treatment at 60° C. for 3 min.

The lysozyme lyzTA expression plasmid was constructed
as follows: primers lyzTte-F and lyzAth-R were used for
PCR amplification to obtain a lyzTA gene with a recombinant arm, and then the lyzTA gene was recombined with the
linearized pGla-amdS plasmid by using Gibson Master Mix
Kit (E2611, New England Biolabs) to obtain a plyzTA-amdS
plasmid, which was sequenced to confirm the sequences.
The map of the constructed plasmid was as shown in FIG.
4. The plasmid could be linearized at an ApaI site and then
used for protoplast transformation.

The relevant primer sequences were as follows:

TABLE 1

Primers in the present invention

| Primer name | Sequence (5'-3') |
|---|---|
| vector-F | CTTGGCGTAATCATGGTCATAGC (SEQ ID NO: 9) |
| vector-R | CGGACCCCTCCGCCAATGGCCTTGCATGCAGGCCTCTGCA (SEQ ID NO:10) |
| amdS-F | CTAGATCTACGCCAGGACCG (SEQ ID NO: 11) |
| amdS-R | ATGACCATGATTACGCCAAGCTTCTGGAAACGCAACCCTG (SEQ ID NO: 12) |
| gla-F | GCCATTGGCGGAGGGGTCCG (SEQ ID NO: 13) |
| gla-R | CGGTCCTGGCGTAGATCTAGATGCATTGAATGACAGTGAT (SEQ ID NO: 14) |
| lyzAth-F | catccccagcatcattacacctcagcaatgttgtaccttcctctcgttgccc (SEQ ID NO: 15) |
| lyzAth-R | aggtgtcagtcaccctctagatctcgagctacagtccaccagcagcgcagatctt (SEQ ID NO: 16) |
| lyzTtc-F | catccccagcatcattacacctcagcaatgcagctctccctcctcgtc (SEQ ID NO: 17) |
| lyzTtc-R | gtgtcagtcaccctctagatctcgagttacaacccaccagcctggcaaatct (SEQ ID NO: 18) |

Figure 1:
FIG. 1 is a map of lysozyme lyzAth expression plasmid.

The lysozyme lyzAth expression plasmid was constructed
as follows: primers lyzAth-F and lyzAth-R were used for
PCR amplification to obtain a lyzAth gene with a recombinant arm, and then the lyzAth gene was recombined with the
linearized pGla-amdS plasmid by using Gibson Master Mix
Kit (E2611, New England Biolabs) to obtain a plyzAth-amdS plasmid, which was sequenced to confirm the
sequences. The map of the constructed plasmid was as
shown in FIG. 1. The plasmid could be linearized at an ApaI
site and then used for protoplast transformation.

Figure 2:
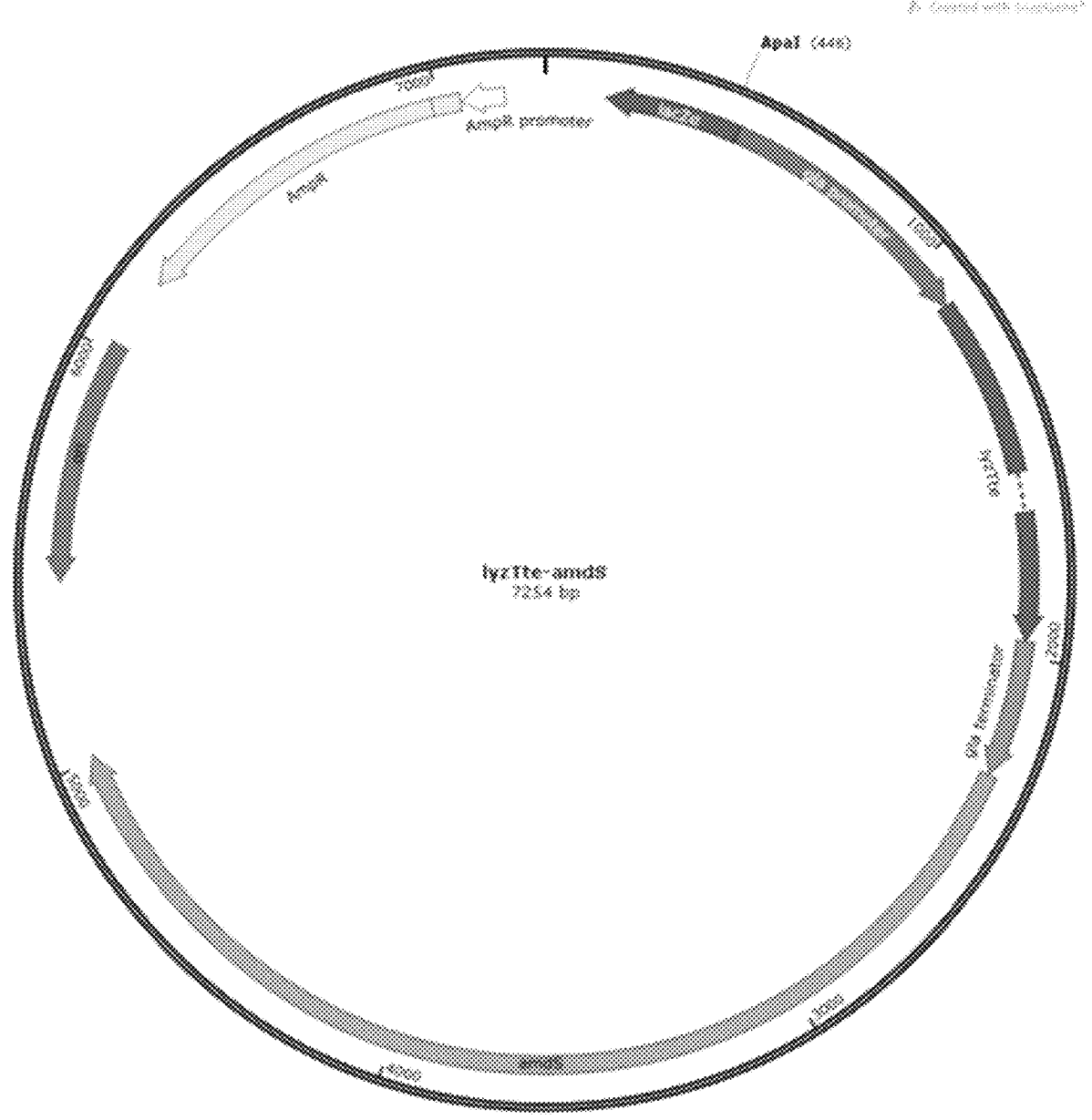
FIG. 2 is a map of lysozyme lyzTte expression plasmid.

The lysozyme lyzTte expression plasmid was constructed
as follows: primers lyzTte-F and lyzTte-R were used for
PCR amplification to obtain a lyzTte gene with a recombinant arm, and then the lyzTte gene was recombined with the
linearized pGla-amdS plasmid by using Gibson Master Mix
Kit (E2611, New England Biolabs) to obtain a plyzTte-amdS plasmid, which was sequenced to confirm the
sequences. The map of the constructed plasmid was as
shown in FIG. 2. The plasmid could be linearized at an ApaI
site and then used for protoplast transformation.

Example 2. Transformation and Integration of
Lysozyme Expression Plasmids plyzAth-amdS,
plyzTte-amdS, plyzAT-amdS and plyzTA-amdS Four linearized lysozyme expression plasmids were introduced into strains of *Aspergillus niger* CICC2462 (purchased from China Center of Industrial Culture Collection,
CICC) by using a protoplast transformation method, respectively, and the specific operation steps were as follows:

(1) Preparation of protoplasts: the mycelium of *Aspergillus niger* was inoculated in a nutritious TZ liquid culture
medium (beef extract powder 0.8%, yeast extract 0.2%,
peptone 0.5%, NaCl 0.2%, and sucrose 3%, pH 5.8), cultured for 48 h, and then filtered with Mira-cloth (Calbiochem
company) to collect the mycelium, and washed with 0.7 M
NaCl (pH 5.8); the washed mycelium was filtered to dryness, and then transferred to an enzymolysis solution (pH
5.8) containing cellulase 1% (Sigma), snail enzyme 1%
(Sigma) and lywallzyme 0.2% (Sigma) for enzymolysis at 30° C. and 65 rpm for 3 h; subsequently, the enzymolysis solution containing protoplasts was placed on ice and filtered through four layers of lens paper; the resulting filtrate was gently centrifuged at 3000 rpm and 4° C. for 10 min, and then the supernatant was discarded; and the protoplasts attached to the tube wall were washed once with an STC solution (1 M D-Sorbitol, 50 mM CaCl$_2$, and 10 mM Tris, pH 7.5), and finally, the protoplasts were resuspended in an appropriate amount of the STC solution.

(2) Transformation of protoplasts: 10 µl (concentration: 1000 ng/µl) of the lysozyme expression plasmid linearized with ApaI was added to 100 µl of the protoplast suspension and mixed well; the mixture was placed at room temperature for 25 min, and then 900 µl of a PEG solution in total was added in three times and mixed well; the mixture was placed at room temperature for 25 min, and then centrifuged at room temperature at a rotating speed of 3000 rpm for 10 min, and the supernatant was discarded; the protoplasts attached to the tube wall were resuspended in 1 ml of the STC solution, mixed with an acetamide culture medium (sucrose 3%, KCl 0.05%, K$_2$HPO$_4$·3H$_2$O 0.1%, FeSO$_4$ 0.001%, MgSO$_4$ 0.0244%, acetamide 0.06%, and CsCl 0.34%) precooled to about 45° C., and spread on a plate; the plate was solidified, and then placed in a 34° C. incubator for 4-5 days; the transformants were picked into a new acetamide culture medium plate and placed in a 34° C. incubator for additional 4-5 days; and the grown transformants were called positive transformants.

Four linearized lysozyme expression plasmids lyzAth-amdS, lyzTte-amdS, lyzAT-amdS and lyzTA-amdS were transformed into strains of *Aspergillus niger* by using the above-mentioned protoplast transformation method, respectively, so as to obtain four lysozyme positive transformants.

Example 3. Shake Flask Culture of Recombinant Expression Strain Formed by Lysozyme and *Aspergillus niger*

The four lysozyme positive transformants as described above were inoculated into a shake flask containing 50 ml of a YPM medium (yeast extract 0.2%, peptone 0.2%, and maltose 2%), respectively, and cultured on a shaker at a temperature of 34° C. and a rotating speed of 220 rpm for 5 days. The cultures were centrifuged to collect a supernatant of the fermentation broth, and the enzyme activity of the lysozyme was determined.

Example 4. Determination of Lysozyme Activity

The lysozyme activity was determined according to the national standard GB/T 1886.257-2016.

Lysozyme can hydrolyze the cell wall of bacteria, leading to the lysis of *Micrococcus luteus* cell walls and consequently a decrease in the absorbance value of the solution. One unit of lysozyme activity is defined as the amount of lysozyme required to cause a change in absorbance of 0.001 per minute at 450 nm using a *Micrococcus luteus* suspension at 25° C. and pH 6.2.

Reagents and Materials

*Micrococcus luteus*: CICC10680 (purchased from China Center of Industrial Culture Collection, CICC).

0.1 mol/L phosphate buffer (pH 6.2).

11.70 g of sodium dihydrogen phosphate (NaH$_2$PO$_4$·2H$_2$O), 7.86 g of disodium hydrogen phosphate (Na$_2$HPO$_4$·12H$_2$O) and 0.372 g of disodium ethylenediamine tetra-acetic acid (EDTA-2Na) were weighed and added to sterile water, and the mixture was diluted to a constant volume of 1000 mL. The buffer solution was adjusted to pH 6.2±0.1.

Lysozyme standard: egg white lysozyme.

Substrate solution: 50 mL of *Micrococcus luteus* suspension was prepared from the phosphate buffer. Before use, the substrate was incubated at 37° C. for 30 min.

The substrate solution could be stable for 2 h at room temperature. The spectrophotometer was adjusted to zero point with the phosphate buffer, and then the absorbance of the substrate solution was determined. The reading at 450 nm should be 0.70±0.1.

Preparation of Standard Solution:

50 mg of egg white lysozyme standard was accurately weighed and added into a 50 mL volumetric flask, and dissolved in about 25 mL of the phosphate buffer with stirring. The mixture was diluted to a constant volume, and mixed thoroughly (if necessary, the solution was frozen for subsequent determination). 3 mL of the above standard preparation solution was transferred to a 100 mL volumetric flask, and dissolved in the phosphate buffer with stirring, and the mixture was diluted to a constant volume.

Determination:

3 standard solutions and 3 sample solutions were taken for determination. At room temperature of 25° C., a 1 cm cuvette was put into a spectrophotometer, and the spectrophotometer was adjusted to zero absorbance with the phosphate buffer. 2.9 mL of substrate solution was pipetted into the cuvette, and the initial absorbance at 450 nm should be 0.70±0.10. The determination could only be started when the change in the initial absorbance value within 3 min was less than or equal to 0.003. 0.1 mL of standard solution was pipetted into the substrate solution and mixed thoroughly. Changes in the absorbance value within 3 min were recorded, and the absorbance value was recorded every 15 s. The changes in the absorbance value per minute should be within 0.03-0.08, and if it went beyond this required range, the concentration of the sample solution should be adjusted. The operation was repeated to determine the sample solution. The reading in the first 1 min should be omitted in the calculation as the reaction became stable after 1 min.

Result Calculation

The enzyme activity X was calculated according to equation (A.1):

$$X = \frac{(A_1 - A_2)}{2 \times m \times 0.001} \tag{A.1}$$

In the equation:

A$_1$: the absorbance of the sample at 450 nm upon 1 min of reaction;

A$_2$: the absorbance of the sample at 450 nm upon 3 min of reaction;

m: the mass of lysozyme in the sample solution used for analysis, expressed in milligram (mg);

2: the time taken to obtain absorbance readings at 1 min and 3 min, expressed in minutes (min);

0.001: the value of the decrease in absorbance per minute caused by one unit of lysozyme.

Example 5. Determination of Heat Resistance of Lysozyme

The lysozyme sample to be tested was diluted to 5000 U/mL using the phosphate buffer. 4.5 mL of the phosphate buffer was added into a test tube, and preheated for 5 min at different temperatures. 0.5 mL of diluent was added to the test tube, and mixed evenly. The mixture was treated in water bath at 60° C. for 3 min, and taken out and then cooled down to room temperature in ice water bath. The cooled mixture was determined for enzyme activity according to the lysozyme activity determination method. Calculation: the residual activity of heat-resistance enzyme as percent of the initial activity $(\%)=U_X/U_0*100\%$, where $U_0$ is the enzyme activity before water bath treatment, and $U_X$ is the enzyme activity after water bath treatment. The determination results were as shown in FIG. 4. The residual activity of Lysozyme lyzAth derived from *Aspergillus thermomutatus* and lysozyme lyzTte derived from *Thermothielavioides terrestris* were 8% and 26%, respectively, after being treated in water bath at 60° C. for 3 min; while the constructed hybrid lysozyme lyzAT is 60% under the same conditions, suggesting that the heat resistance was greatly improved compared to a parental sequence; further, the residual activity of the constructed hybrid lysozyme lyzTA is only 25% under the same conditions, which was close to the heat resistance of the parental lysozyme lyzTte.

TABLE 2

Determination of residual heat-resistance enzyme activity of lysozyme

| Lysozyme | $U_0$ (U/mL) | $U_X$ (U/mL) | Residual activity of heat-resistance enzyme as percent of the initial activity (%) |
|---|---|---|---|
| lyzAth | 53710 | 4250 | 8 |
| lyzTte | 101310 | 26140 | 26 |
| lyzAT | 220000 | 131220 | 60 |
| lyzTA | 138120 | 35110 | 25 |

Example 6

1. Test Materials

Test animals: Arbor Acres (AA) male broilers.

Enzyme for test: lysozyme lyzAT (500,000 U/g, detected by the national standard method) having an amino acid sequence set forth in SEQ ID NO: 8.

2. Test Design 700 1-day-old healthy Arbor Acres (AA) male broilers were selected and randomly divided into 5 treatment groups, with no significant difference in average weight among the treatment groups. 14 replicates were set for each treatment group, with 10 broilers in each replicate. The 5 treatment groups were divided into 1 control group and 4 test groups, and the addition amounts of lysozyme lyzAT in the control group and each test group were as follows, respectively: 0, 250 g/t, 500 g/t, 1000 g/t and 3000 g/t.

The test period lasted for 42 days in total, and consisted of two stages: early stage and late stage.

3. Test Diet and Nutritional Level

In this test, corn-soybean meal basal diet was selected and formulated separately according to 2 stages of the 0-21-day-old stage and the 22-42-day-old stage as guided by Nutritional Requirements of Chicken of NRC (1994), Feeding Standard of Chicken in China (2004) and Tables of Feed Composition and Nutritive Values in China (2020). The composition and nutritional level of the basal diet were as shown in Table 3.

TABLE 3

Formula and nutritional level % (air-dried basis) of basal diet

| Item | 0-21-day-old | Item | 22-42-day-old |
|---|---|---|---|
| Raw material | | Raw material | |
| Corn | 56.76 | Corn | 57.92 |
| Dehulled soybean meal | 26.5 | Dehulled soybean meal | 26 |
| Corn gluten meal | 3.2 | Corn gluten meal | 3 |
| Fine stone powder | 1.1 | Fine stone powder | 1.1 |
| Calcium hydrogen phosphate | 1.1 | Calcium hydrogen phosphate | 1.1 |
| Chicken oil | 6.5 | Chicken oil | 6 |
| Glutamic acid residue | 2 | Glutamic acid residue | 2 |
| Feather meal | 0.5 | Feather meal | 0.5 |
| Sodium chloride | 0.28 | Sodium chloride | 0.28 |
| Lysine 70% | 0.78 | Lysine 70% | 0.77 |
| Methionine 99% | 0.22 | Threonine 98.5% | 0.1 |
| Enzymemate B | 0.05 | Methionine 99% | 0.2 |
| Glucose oxidase | 0.01 | Enzymemate B | 0.02 |
| Premix 1) | 1 | Glucose oxidase | 0.01 |
| Premix 1) | 1 | | |
| Total | 100 | Total | 100 |
| Nutritional level | | | |
| Metabolic energy (MJ/kg) 2) | 11.42 | | 13.49 |
| Crude protein | 20.0 | | 20.5 |
| Crude fat | 4.21 | | 5.51 |
| Calcium | 0.97 | | 0.77 |
| Phosphorus | 0.41 | | 0.32 |

Notes:
in Table 3:
1) Premix provides the following per kilogram of diet: $VD_3$ 2 750 IU, VE 20 IU, $VK_3$ 2 mg, $VB_1$ 1.5 mg, $VB_2$ 6 mg, pantothenic acid 12 mg, nicotinic acid 20 mg, $VB_6$ 2.5 mg, $VB_{12}$ 2.03 mg, Mn 75 mg, Zn 75 mg, Fe 95 mg, Cu 10 mg, I 0.6 mg, and Se 0.3 mg.
2) Metabolic energy is a calculated value, and the rest is a measured value.
4. Feeding management The test was carried out in the experimental chicken farm of Shenyang Agricultural University. Before the test, the surrounding environment, chicken houses and tools to be used were disinfected. Chickens to be tested were raised in three-dimensional cages, and 14 replicates in each group were arranged separately according to the different positions of the cages, so that the test conditions of each group remained the same except for the test parameters of different lysozyme products and doses. Chickens were given free access to food and water, and raised under free ventilation and all-day illumination. Feeding management and immunization were carried out according to normal procedures, and data collection and recording were made on time.

5. Determination Indicators 5.1 Production Performance

During the feeding test, the feed given and the feed consumption were recorded every day, and broilers in each replicate were weighed on an empty stomach on d1, d21 and d42 of the test, so as to calculate the average daily feed intake (ADFI), average daily gain (ADG) and feed-to-gain ratio (F/G) in each stage and the whole growth period. Death cases were observed and recorded carefully every day, so as to calculate the mortality.

The average daily feed intake, average daily gain, feed-to-gain ratio and mortality are calculated as follows:

average daily feed intake (ADFI)=feed consumption in each treatment group during the test period/ (test days×number of broilers in each treatment group);

average daily gain (ADG)=weight gain in each treatment group during the test period/(test days× number of broilers in each treatment group);

feed-to-gain ratio (F/G)=average daily feed intake/ average daily gain;

mortality (%)=number of mortal broilers at the end of the test/number of broilers at the beginning of the test×100%.

5.2 European Index

The European index is a comprehensive evaluation of the weight, survival rate, feed-to-gain ratio, production management and other indicators of broilers, which reflects the level of profitability. The larger the index, the more profitable it is. The European index is calculated as follows:

European index=survival rate×weight (kg)/(feed-to-meat ratio×days to market)×10000.

5.3 Calculation of Economic Benefit Indicator

The comprehensive economic benefit is equal to the sales price of broilers minus the production cost of broilers, in which the main factors affecting the production cost of broilers are the feed-to-meat ratio, the average feed price and the cost of baby chicks; in addition, the market price of broilers when they are marketed also has a great influence on the economic benefit of broiler feeding.

According to the feed consumption, growth conditions and other data, the comprehensive economic benefits of the control group and the test groups were compared.

5.4 Data Processing and Statistical Analysis

Recording and arrangement of test data: EXCEL software was used for data processing and analysis, and SPSS 17.0 software was used for one-way ANOVA. When the differences were significant, a Dun-can method was used for multiple comparison, with P<0.05 as the significant level and P<0.01 as the extremely significant level, and the results were expressed as "mean±standard deviation".

Results and Analysis

1. Effect of Lysozyme lyzAT on Production Performance of Broilers

As could be seen from the Table 4, at the 0-21-day-old stage, the final weight of broilers in test groups of lysozyme lyzAT 500 g/t and 1000 g/t was significantly higher than that in the control group (P<0.05), but there was no significant difference between the remaining test groups and the control group (P>0.05); the average daily gain of broilers in test groups of lysozyme lyzAT 500 g/t and 1000 g/t was significantly higher than that in the control group (P<0.05), but there was no significant difference between the remaining test groups and the control group (P>0.05); with respect to the feed-to-gain ratio, test groups all showed a decreasing trend compared with the control group (P=0.089), with a decrease of 1.55% in test groups of lysozyme lyzAT 250 g/t, 500 g/t and 1000 g/t; and there was no significant difference in the average daily feed intake between test groups and the control group (P>0.05).

At the 22-42-day-old stage, the final weight of broilers in the test group of lysozyme lyzAT 250 g/t was extremely significantly higher than that in the control group (P<0.01), and the final weight of broilers in the test group of lysozyme lyzAT 500 g/t was significantly higher than that in the control group (P<0.05), but there was no significant difference between the remaining test groups and the control group (P>0.05); the average daily gain in test groups of lysozyme lyzAT 250 g/t and 500 g/t was extremely significantly higher than that in the control group (P<0.01), and the average daily gain in the test group of 1000 g/t was significantly higher than that in the control group (P<0.05), but there was no significant difference between the test group of 3000 g/t and the control group (P>0.05); the feed-to-gain ratio in test groups of lysozyme lyzAT 250 g/t and 500 g/t was significantly lower than that in the control group (P<0.05), but there was no significant difference between the remaining test groups and the control group (P>0.05); and with respect to the average daily feed intake, there was an increasing trend in test groups compared with the control group (P=0.075), and the test group of lysozyme lyzAT 500 g/t showed an increase of 2.50% compared with the control group.

At the whole 0-42-day-old stage, the average daily gain in test groups of lysozyme lyzAT 250 g/t, 500 g/t and 1000 g/t was all extremely significantly higher than that in the control group (P<0.01); the feed-to-gain ratio in the test group of lysozyme lyzAT 250 g/t was extremely significantly lower than that in the control group (P<0.01), and the feed-to-gain ratio in the test group of lysozyme lyzAT 500 g/t was significantly lower than that in the control group (P<0.05); and there was no significant difference in the average daily feed intake among the test groups (P>0.05).

TABLE 4

Effect of lysozyme lyzAT on production performance of broilers

| Item | Age in days | Control group | 250 g/t | 500 g/t | 1000 g/t | 3000 g/t | P value |
|---|---|---|---|---|---|---|---|
| | | | Treatment group | | | | |
| Weight (g) | 0 | 38.00 | 38.00 | 38.00 | 38.00 | 38.00 | |
| | 21 | 855.35 ± 7.19$^b$ | 857.85 ± 6.71$^{ab}$ | 862.14 ± 6.99$^a$ | 862.85 ± 8.01$^a$ | 860.35 ± 6.64$^{ab}$ | 0.040 |
| | 42 | 2558.92 ± 53.12$^{Bc}$ | 2708.64 ± 83.16$^{Aa}$ | 2632.11 ± 60.30$^{Bb}$ | 2596.45 ± 70.43$^{Bbc}$ | 2616.07 ± 73.41$^{Bbc}$ | 0.000 |
| Average daily gain (g) | 0-21 | 38.91 ± 0.34$^b$ | 39.03 ± 0.31$^{ab}$ | 39.24 ± 0.33$^a$ | 39.27 ± 0.38$^a$ | 39.15 ± 0.31$^{ab}$ | 0.039 |
| | 22-42 | 81.19 ± 2.69$^{Cc}$ | 87.69 ± 3.91$^{Aa}$ | 87.29 ± 4.66$^{ABa}$ | 84.73 ± 5.05$^{ABCab}$ | 83.18 ± 3.32$^{BCbc}$ | 0.000 |
| | 0-42 | 59.80 ± 1.31$^{Cc}$ | 63.58 ± 1.98$^{Aa}$ | 63.27 ± 2.38$^{ABa}$ | 62.05 ± 12.50$^{ABab}$ | 61.38 ± 1.74$^{BCb}$ | 0.000 |
| Average daily feed intake (g) | 0-21 | 50.19 ± 0.61 | 49.82 ± 0.51 | 49.93 ± 0.47 | 50.16 ± 0.45 | 50.12 ± 0.49 | 0.261 |
| | 22-42 | 124.95 ± 2.21 | 126.19 ± 2.56 | 128.07 ± 3.41 | 126.91 ± 3.53 | 125.72 ± 2.96 | 0.075 |
| | 0-42 | 87.57 ± 1.17 | 88.29 ± 1.57 | 89.01 ± 1.74 | 88.53 ± 1.86 | 87.92 ± 1.43 | 0.155 |

TABLE 4-continued

| | | Treatment group | | | | |
|---|---|---|---|---|---|---|
| Item | Age in days | Control group | 250 g/t | 500 g/t | 1000 g/t | 3000 g/t | P value |
| Feed-to-gain ratio | 0-21 | 1.29 ± .0.02 | 1.27 ± 0.01 | 1.27 ± 0.01 | 1.27 ± 0.02 | 1.28 ± 0.02 | 0.089 |
| | 22-42 | 1.54 ± 0.05$^a$ | 1.44 ± 0.07$^c$ | 1.47 ± 0.09$^{bc}$ | 1.50 ± 0.11$^{abc}$ | 1.51 ± 0.05$^{ab}$ | 0.021 |
| | 0-42 | 1.45 ± 0.03$^{Aa}$ | 1.38 ± 0.04$^{Bc}$ | 1.40 ± 0.06$^{ABbc}$ | 1.43 ± 0.07$^{ABab}$ | 1.43 ± 0.03$^{ABab}$ | 0.007 |

Effect of lysozyme lyzAT on production performance of broilers

Notes:

different lowercase letters occurring as the superscript of data in the same row indicate significant differences (P < 0.05); capital letters indicate extremely significant differences (P < 0.01); and the same letters or no letters indicate no significant differences (P > 0.05).

2. Effect of Lysozyme lyzAT on European Index of Broilers

As could be seen from Table 5, the European index of the control group was the lowest compared with all the test groups throughout the test, and the European index of the test group of lysozyme lyzAT 250 g/t was the highest throughout the test, which was 62.58 higher than that of the control group, indicating that adding lysozyme can improve the profitability of broilers.

TABLE 5

Effect of lysozyme lyzAT on European index of broilers

| | | Treatment group | | | |
|---|---|---|---|---|---|
| Item | Control group | 250 g/t | 500 g/t | 1000 g/t | 3000 g/t |
| Lysozyme A | 385.50 | 448.08 | 422.96 | 412.70 | 407.21 |

3. Effect of Lysozyme lyzAT on Breeding Benefit of Broilers

The price of chicks is 1.95 yuan/chick; the price of commercial live chickens is 8.4 yuan/kg; and the price of feeds is 3,500 yuan/t. As could be seen from Table 6, the average profit per chicken of all test groups of lysozyme lyzAT was higher than that of the control group, with the average profit per chicken of the test group of lysozyme lyzAT 250 g/t being the highest, which was 1.08 yuan higher than that of the control group.

TABLE 6

Effect of lysozyme lyzAT on breeding benefit of broilers

| | | | Treatment group | | | |
|---|---|---|---|---|---|---|
| Item | Age in days | Control group | 250 g/t | 500 g/t | 1000 g/t | 3000 g/t |
| Lysozyme lyzAT | Average weight gain per chicken (kg) | 2.52 | 2.67 | 2.59 | 2.56 | 2.58 |
| | Average weight gain benefit per chicken (yuan) | 21.17 | 22.43 | 21.76 | 21.50 | 21.67 |
| | Average feed consumption per chicken (yuan) | 12.52 | 12.71 | 12.42 | 12.45 | 12.64 |
| | Average profit per chicken (yuan) | 6.69 | 777 | 7.39 | 7.10 | 7.08 |

Therefore, it can be seen from the above test data that the feed with lysozyme lyzAT added can significantly improve the weight, average daily gain and average daily feed intake of broilers at all stages, and at the same time can significantly reduce the feed-to-gain ratio. Additionally, the remarkable improvement of the European index and economic benefit indicators also shows that the breeding benefit of lysozyme lyzAT is rather considerable, and the addition amount of the lysozyme can be 100-1000 g/t, with the most suitable addition amount being 250-500 g/t.

The content of protection of the present invention is not limited to the above examples. Without departing from the spirit and scope of the present invention, variations and advantages that can be conceived by those skilled in the art are all included in the present invention, and the scope of protection shall be in accordance with the appended claims.

What is claimed is:

1. A chimeric lysozyme variant, wherein the chimeric lysozyme variant has an amino acid sequence set forth in SEQ ID NO: 8, or has at least 90%, at least 91%, at least 92%, at least 93%, at least 94%, at least 95%, at least 96%, at least 97%, at least 98%, or at least 99% sequence identity to SEQ ID NO: 8; and wherein the chimeric lysozyme variant has a lysozyme activity and exhibits increased thermostability as compared to a lysozyme of SEQ ID NO: 4 or SEQ ID NO: 6.

2. The chimeric lysozyme variant of claim 1, wherein the chimeric lysozyme variant has an amino acid sequence set forth in SEQ ID NO: 8.

3. A method of substituting an antibiotic in an animal, comprising administering to the animal an effective amount of the chimeric lysozyme variant of claim 1.

4. A polynucleotide, wherein the polynucleotide encodes the chimeric lysozyme variant of claim 1.

5. The polynucleotide of claim 4, wherein the polynucleotide has a nucleotide sequence set forth in SEQ ID NO: 7.

6. A recombinant vector, wherein the recombinant vector contains the polynucleotide of claim 4.

7. A host cell, wherein the host cell contains the recombinant vector of claim 6.

8. The host cell of claim 7, wherein the host cell is selected from any of the *Aspergillus niger, Pichia pastoris, Aspergillus oryzae, Trichoderma reesei, Bacillus subtilis, Bacillus licheniformis* or *Escherichia coli.*

9. An animal feed additive, wherein the animal feed additive comprises the chimeric lysozyme variant of claim 1.

10. The animal feed additive of claim 9, wherein the chimeric lysozyme variant is added in an amount of 100-1000 g chimeric lysozyme variant per ton of animal feed.

11. The animal feed additive of claim 10, wherein the chimeric lysozyme variant is added in an amount of 250-500 g chimeric lysozyme variant per ton of animal feed.

12. A method for improving one or more performance parameters of an animal, comprising administering to the animal a feed or feed additive comprising the chimeric lysozyme variant of claim 1, wherein the performance parameters comprise weight gain or feed conversion rate of the animal.

* * * * *